(12) United States Patent
Enmark et al.

(10) Patent No.: US 6,525,188 B2
(45) Date of Patent: Feb. 25, 2003

(54) NUCLEAR RETINOIC ACID CO-RECEPTOR

(75) Inventors: Eva L. K. Enmark, Tullinge (SE); Jan-Ake Gustafsson, Stockholm (SE)

(73) Assignee: Karo Bio Ab, Huddinge (SE)

( * ) Notice: Subject to any disclaimer, the term of this patent is extended or adjusted under 35 U.S.C. 154(b) by 14 days.

(21) Appl. No.: 09/909,325

(22) Filed: Jul. 19, 2001

(65) Prior Publication Data

US 2002/0115847 A1 Aug. 22, 2002

Related U.S. Application Data

(63) Continuation of application No. 08/776,844, filed as application No. PCT/EP95/03247 on Aug. 16, 1995, now Pat. No. 6,277,976.

(30) Foreign Application Priority Data

Aug. 16, 1994 (GB) ............................................. 9416536

(51) Int. Cl.[7] ............................................... C12N 15/12
(52) U.S. Cl. .................. 536/23.5; 435/69.1; 435/252.3; 435/320.1
(58) Field of Search .............................. 435/69.1, 252.3, 435/320.1; 536/23.5

(56) References Cited

U.S. PATENT DOCUMENTS 5,639,616 A    6/1997    Liao et al. .................... 435/7.1

FOREIGN PATENT DOCUMENTS

WO    93-06215    4/1993
WO    95-13373    5/1995

OTHER PUBLICATIONS

Ayala et al., Modern Genetics, 45–48, 1980 Benjamin/Cummings Publishing Company Inc., Menlo Park, California.

George et al., Macromolecular Sequencing and Synthesis, Selected Methods and applications, 127–149, 1988, Alan R. Liss, Inc.

Song, Ching; Characterization Of A Unbiquitous Receptor, A New Member Of The Nuclear Receptor Superfamily; University of Chicago;(1994) Diss. Abstract. Int. B., 1994; 55(3), 734.

Tebol, M. et al., "OR–1, A Member Of The Nuclear Receptor Superfamily That Interacts With The 9–Cis–Retinoic Acid Receptor" Proc. Natl. Acad. Sci. USA 92:2096–2100 (Mar. 14, 1995).

*Primary Examiner*—John Ulm
(74) *Attorney, Agent, or Firm*—Todd E. Garabedian; Wiggin & Dana LLP

(57) ABSTRACT

This invention provides an isolated receptor having the amino acid sequence of FIG. 1 (SEQ ID NO:2) or substantially the same amino acid sequence as the amino acid sequence shown in FIG. 1 (SEQ ID NO:2) or an amino acid sequence functionally similar to that sequence, and DNA sequences encoding such a receptor.

2 Claims, 8 Drawing Sheets

| | |
|---|---|
| 1 | MSSPTSSLDT PLPGNGSPQP STSSTSPTIK EEGQETDPPP GSEGSSSAYI |
| 51 | VVILEPEDEP ERKRKKGPAP KMLGHELCRV CGDKASGFHY NVLSCEGCKG |
| 101 | FFRRSVVHGG AGRYACRGSG TCQMDAFMRR KCQLCRLRKC KEAGMREQCV |
| 151 | LSEEQIRKKK IQKQQQQQPP PPTEPASGSS ARPAASPGTS EASSQGSGEG |
| 201 | EGIQLTAAQE LMIQQLVAAQ LQCNKRSFSD QPKVTPWPLG ADPQSRDARQ |
| 251 | QRFAHFTELA IISVQEIVDF AKQVPGFLQL GREDQIALLK ASTIEIMLLE |
| 301 | TARRYNHETE CITFLKDFTY SKDDFHRAGL QVEFINPIFE FSRAMRRLGL |
| 351 | DDAEYALLIA INIFSADRPN VQEPSRVEAL QQPYVEALLS YTRIKRPQDQ |
| 401 | LRFPRMLMKL VSLRTLSSVH SEQVFALRLQ DKKLPPLLSE IWDVHE* |

*FIG. 1*

```
   1    CAAGTGCTGT GGAGGAGCAA TCACCGGTGC GGACACAGAG CTCCCGCCTC
  51    CCACAGCCAT TTCCAGGGTA ACGAAGTAGG AGACCCCCTC CTGCGACCCC
 101    CTCACGATCG CCGGTGCAGT CATGAGCCCC GCCTCCCCCT GGTGCACGGA
 151    GAGGGGCGGG GCCTGGAACG AGGCTGCTTC GTGACCCACT ATGTCTTCCC
 201    CCACAAGTTC TCTGGACACT CCCTTGCCTG GAATGGTTC TCCCCAGCCC
 251    AGTACCTCCT CCACTTCACC CACTATTAAG GAGGAGGGAC AGGAGACTGA
 301    TCCACCTCCA GGCTCTGAAG GGTCCAGCTC TGCCTACATC GTGGTCATCT
 351    TAGAGCCAGA GGATGAACCT GAGCGCAAGC GGAAGAAGGG TCCGGCCCCG
 401    AAGATGCTGG GCCATGAGCT GTGCCGCGTG TGCGGGGACA AGGCCTCGGG
 451    CTTCCACTAC AATGTGCTCA GTTGTGAAGG CTGCAAAGGC TTCTTCCGGC
 501    GTAGCGTGGT CCATGGTGGG GCCGGGCGCT ATGCCTGTCG GGGCAGCGGA
 551    ACCTGCCAGA TGGATGCCTT CATGCGGCGC AAGTGCCAGC TCTGCAGACT
 601    GCGCAAGTGC AAGGAGGCTG GCATGCGGGA GCAGTGCGTG CTTTCTGAGG
 651    AGCAGATTCG GAAGAAAAAG ATTCAGAAGC AGCAACAGCA GCAGCCACCG
 701    CCCCCGACTG AGCCAGCATC CGGTAGCTCA GCCCGGCCTG CAGCCTCCCC
 751    TGGCACTTCG GAAGCAAGTA GCCAGGGCTC CGGGGAAGGA GAGGGCATCC
 801    AGCTGACAGC GGCTCAGGAG CTGATGATCC AACAGTTAGT TGCCGCGCAG
 851    CTGCAGTGCA ACAAGCGATC TTTCTCCGAC CAGCCTAAAG TCACGCCCTG
 901    GCCCTTGGGT GCAGACCCTC AGTCCCGAGA CGCTCGTCAG CAACGCTTTG
 951    CCCACTTCAC TGAGCTAGCC ATCATCTCAG TCCAGGAGAT CGTGGACTTC
1001    GCCAAGCAGG TGCCAGGGTT CCTGCAGCTG GGCCGGGAGG ACCAGATCGC
1051    CCTCCTGAAG GCATCCACCA TCGAGATCAT GTTGCTAGAG ACAGCCAGAC
1101    GCTACAACCA CGAGACAGAG TGCATCACGT TCCTGAAGGA CTTCACCTAC
```

*FIG. 2A*

```
1151    AGCAAGGACG ACTTCCACCG TGCAGGCTTG CAGGTGGAGT TCATCAATCC
1201    CATCTTTGAG TTCTCTCGGG CTATGCGTCG GCTGGGCCTA GACGATGCAG
1251    AGTATGCCTT GCTCATTGCC ATCAACATCT TCTCAGCGGA CCGGCCTAAT
1301    GTGCAGGAGC CCAGCCGTGT GGAGGCTCTG CAGCAGCCCT ATGTGGAGGC
1351    CCTCCTCTCC TACACGAGGA TCAAGCGGCC GCAGGACCAG CTGCGCTTCC
1401    CACGAATGCT CATGAAGCTG GTGAGCCTGC GCACCCTCAG CTCCGTGCAC
1451    TCGGAGCAGG TTTTCGCATT GCGTCTCCAG GACAAGAAGC TGCCGCCTTT
1501    GCTGTCCGAG ATCTGGGATG TGCATGAGTA GGGGCCGCCA CAAGTGCCCC
1551    AGCCTTGGTG GTGTCTACTT GCAGATGGAC GCTTCCTTTG CCTTTCCTGG
1601    GGTGGGAGGA CACTGTCACA GCCCAGTCCC CTGGGCTCGG GCTGAGCGAG
1651    TGGCAGTTGG CACTAGAAGG TCCCACCCCA CCCGCTGAGT CTTCCAGGAG
1701    TGGTGAGGGT CACAGGCCCT AGCCTCTGAT CTTTACCAGC TGCCCTTCCT
1751    CCCGAGCTTA CACCTCAGCC TACCACACCA TGCACCTTGA GTGGAGAGAG
1801    GTTAGGGCAG GTGGCTCCCC ACAGTTGGGA GACCACAGGC CCCCTCTTCT
1851    GCCCCTTTTA TTTAATAAAA AAATAAAATA AAAAAAAAAA AAAAAAAAA
1901    AAAAAAAAAA AAAAAAAAAA AAAAAAAAAA AAAA
```

*FIG. 2B*

DR-0  AGGTCA  AGGTCA

DR-1  AGGTCA  c  AGGTCA

DR-2  AGGTCA  cc  AGGTCA

DR-3  AGGTCA  ctc  AGGTCA

DR-4  AGGTCA  ctcg  AGGTCA

DR-5  AGGTCA  ctcgt  AGGTCA

DR-6  AGGTCA  ctcgtt  AGGTCA

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 1934 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

```
CAAGTGCTGT GGAGGAGCAA TCACCGGTGC GGACACAGAG CTCCCGCCTC CCACAGCCAT    60
TTCCAGGGTA ACGAAGTAGG AGACCCCCTC CTGCGACCCC CTCACGATCG CCGGTGCAGT   120
CATGAGCCCC GCCTCCCCCT GGTGCACGGA GAGGGCGGG GCCTGGAACG AGGCTGCTTC    180
GTGACCCACT ATGTCTTCCC CCACAAGTTC TCTGGACACT CCCTTGCCTG GAATGGTTC    240
TCCCCAGCCC AGTACCTCCT CCACTTCACC CACTATTAAG GAGGAGGGAC AGGAGACTGA   300
TCCACCTCCA GGCTCTGAAG GGTCCAGCTC TGCCTACATC GTGGTCATCT TAGAGCCAGA   360
GGATGAACCT GAGCGCAAGC GGAAGAAGGG TCCGGCCCCG AAGATGCTGG GCCATGAGCT   420
GTGCCGCGTG TGCGGGGACA AGGCCTCGGG CTTCCACTAC AATGTGCTCA GTTGTGAAGG   480
CTGCAAAGGC TTCTTCCGGC GTAGCGTGGT CCATGGTGGG GCCGGGCGCT ATGCCTGTCG   540
GGGCAGCGGA ACCTGCCAGA TGGATGCCTT CATGCGGCGC AAGTGCCAGC TCTGCAGACT   600
GCGCAAGTGC AAGGAGGCTG GCATGCGGGA GCAGTGCGTG CTTTCTGAGG AGCAGATTCG   660
GAAGAAAAAG ATTCAGAAGC AGCAACAGCA GCAGCCACCG CCCCCGACTG AGCCAGCATC   720
CGGTAGCTCA GCCCGGCCTG CAGCCTCCCC TGGCACTTCG GAAGCAAGTA GCCAGGGCTC   780
CGGGGAAGGA GAGGGCATCC AGCTGACAGC GGCTCAGGAG CTGATGATCC AACAGTTAGT   840
TGCCGCGCAG CTGCAGTGCA ACAAGCGATC TTTCTCCGAC CAGCCTAAAG TCACGCCCTG   900
GCCCTTGGGT GCAGACCCTC AGTCCCGAGA CGCTCGTCAG CAACGCTTTG CCCACTTCAC   960
TGAGCTAGCC ATCATCTCAG TCCAGGAGAT CGTGGACTTC GCCAAGCAGG TGCCAGGGTT  1020
CCTGCAGCTG GGCCGGGAGG ACCAGATCGC CCTCCTGAAG GCATCCACCA TCGAGATCAT  1080
GTTGCTAGAG ACAGCCAGAC GCTACAACCA CGAGACAGAG TGCATCACGT TCCTGAAGGA  1140
CTTCACCTAC AGCAAGGACG ACTTCCACCG TGCAGGCTTG CAGGTGGAGT TCATCAATCC  1200
CATCTTTGAG TTCTCTCGGG CTATGCGTCG GCTGGGCCTA GACGATGCAG AGTATGCCTT  1260
GCTCATTGCC ATCAACATCT TCTCAGCGGA CCGGCCTAAT GTGCAGGAGC CCAGCCGTGT  1320
GGAGGCTCTG CAGCAGCCCT ATGTGGAGGC CCTCCTCTCC TACACGAGGA TCAAGCGGCC  1380
GCAGGACCAG CTGCGCTTCC CACGAATGCT CATGAAGCTG GTGAGCCTGC GCACCCTCAG  1440
CTCCGTGCAC TCGGAGCAGG TTTTCGCATT GCGTCTCCAG GACAAGAAGC TGCCGCCTTT  1500
GCTGTCCGAG ATCTGGGATG TGCATGAGTA GGGGCCGCCA CAAGTGCCCC AGCCTTGGTG  1560
GTGTCTACTT GCAGATGGAC GCTTCCTTTG CCTTTCCTGG GGTGGGAGGA CACTGTCACA  1620
GCCCAGTCCC CTGGGCTCGG GCTGAGCGAG TGGCAGTTGG CACTAGAAGG TCCCACCCCA  1680
CCCGCTGAGT CTTCCAGGAG TGGTGAGGGT CACAGGCCCT AGCCTCTGAT CTTTACCAGC  1740
TGCCCTTCCT CCCGAGCTTA CACCTCAGCC TACCACACCA TGCACCTTGA GTGGAGAGAG  1800
```

-continued

```
GTTAGGGCAG GTGGCTCCCC ACAGTTGGGA GACCACAGGC CCCCTCTTCT GCCCCTTTTA    1860

TTTAATAAAA AAATAAAATA AAAAAAAAAA AAAAAAAAAA AAAAAAAAAA AAAAAAAAAA    1920

AAAAAAAAAA AAAA                                                      1934
```

(2) INFORMATION FOR SEQ ID NO: 2:

(i) SEQUENCE CHARACTERISTICS:
        (A) LENGTH: 446 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Ser Ser Pro Thr Ser Ser Leu Asp Thr Pro Leu Pro Gly Asn Gly
 1               5                  10                  15

Ser Pro Gln Pro Ser Thr Ser Ser Thr Ser Pro Thr Ile Lys Glu Glu
                20                  25                  30

Gly Gln Glu Thr Asp Pro Pro Gly Ser Glu Gly Ser Ser Ser Ala
            35                  40                  45

Tyr Ile Val Val Ile Leu Glu Pro Glu Asp Glu Pro Glu Arg Lys Arg
 50                  55                  60

Lys Lys Gly Pro Ala Pro Lys Met Leu Gly His Glu Leu Cys Arg Val
65                  70                  75                  80

Cys Gly Asp Lys Ala Ser Gly Phe His Tyr Asn Val Leu Ser Cys Glu
                85                  90                  95

Gly Cys Lys Gly Phe Phe Arg Arg Ser Val His Gly Gly Ala Gly
            100                 105                 110

Arg Tyr Ala Cys Arg Gly Ser Gly Thr Cys Gln Met Asp Ala Phe Met
            115                 120                 125

Arg Arg Lys Cys Gln Leu Cys Arg Leu Arg Lys Cys Lys Glu Ala Gly
            130                 135                 140

Met Arg Glu Gln Cys Val Leu Ser Glu Glu Gln Ile Arg Lys Lys Lys
145                 150                 155                 160

Ile Gln Lys Gln Gln Gln Gln Pro Pro Pro Thr Glu Pro Ala
                165                 170                 175

Ser Gly Ser Ser Ala Arg Pro Ala Ala Ser Pro Gly Thr Ser Glu Ala
            180                 185                 190

Ser Ser Gln Gly Ser Gly Glu Gly Glu Gly Ile Gln Leu Thr Ala Ala
            195                 200                 205

Gln Glu Leu Met Ile Gln Gln Leu Val Ala Ala Gln Leu Gln Cys Asn
210                 215                 220

Lys Arg Ser Phe Ser Asp Gln Pro Lys Val Thr Pro Trp Pro Leu Gly
225                 230                 235                 240

Ala Asp Pro Gln Ser Arg Asp Ala Arg Gln Gln Arg Phe Ala His Phe
            245                 250                 255

Thr Glu Leu Ala Ile Ile Ser Val Gln Glu Ile Val Asp Phe Ala Lys
            260                 265                 270

Gln Val Pro Gly Phe Leu Gln Leu Gly Arg Glu Asp Gln Ile Ala Leu
            275                 280                 285

Leu Lys Ala Ser Thr Ile Glu Ile Met Leu Leu Glu Thr Ala Arg Arg
            290                 295                 300

Tyr Asn His Glu Thr Glu Cys Ile Thr Phe Leu Lys Asp Phe Thr Tyr
305                 310                 315                 320
```

```
Ser Lys Asp Asp Phe His Arg Ala Gly Leu Gln Val Glu Phe Ile Asn
            325                 330                 335

Pro Ile Phe Glu Phe Ser Arg Ala Met Arg Arg Leu Gly Leu Asp Asp
            340                 345                 350

Ala Glu Tyr Ala Leu Leu Ile Ala Ile Asn Ile Phe Ser Ala Asp Arg
            355                 360                 365

Pro Asn Val Gln Glu Pro Ser Arg Val Glu Ala Leu Gln Gln Pro Tyr
        370                 375                 380

Val Glu Ala Leu Leu Ser Tyr Thr Arg Ile Lys Arg Pro Gln Asp Gln
385                 390                 395                 400

Leu Arg Phe Pro Arg Met Leu Met Lys Leu Val Ser Leu Arg Thr Leu
            405                 410                 415

Ser Ser Val His Ser Glu Gln Val Phe Ala Leu Arg Leu Gln Asp Lys
            420                 425                 430

Lys Leu Pro Pro Leu Leu Ser Glu Ile Trp Asp Val His Glu
            435                 440                 445

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

AGCTTCAGGT CAAGGTCAGG TTCA                                          24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AGCTTCAGGT CACAGGTCAG TTCA                                          24

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

AGCTTAGGTC ACCAGGTCAG TTCA                                          24

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 6:

AGTCCAGGTC ACTCAGGTCA GTCA                                    24

(2) INFORMATION FOR SEQ ID NO: 7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

AGTCAGGTCA CTCGAGGTCA GTCA                                    24

(2) INFORMATION FOR SEQ ID NO: 8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA to scRNA (xi) SEQUENCE DESCRIPTION: SEQ ID NO: 8:

AGTCAGGTCA CTCGTAGGTC AGTCA                                   25

(2) INFORMATION FOR SEQ ID NO: 9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 9:

AGTCAGGTCA CTCGTTAGGT CAGTCA                                  26

(2) INFORMATION FOR SEQ ID NO: 10:

(i) SEQUENCE CHARACTERISTICS:
            (A) LENGTH: 6 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 10:

AGGTCA                                                         6

(2) INFORMATION FOR SEQ ID NO: 11:

(i) SEQUENCE CHARACTERISTICS:
            (A) LENGTH: 24 base pairs
            (B) TYPE: nucleic acid
            (C) STRANDEDNESS: double
            (D) TOPOLOGY: linear

```
    (ii) MOLECULE TYPE: cDNA (xi) SEQUENCE DESCRIPTION: SEQ ID NO: 11:

AGTCAGGTCA CTCGAGGTCA GTCA                                              24
```

NUCLEAR RETINOIC ACID CO-RECEPTOR

CROSS-REFERENCE TO RELATED APPLICATIONS

This application is a Continuation application of U.S. Ser. No. 08/776,844 filed Jun. 24, 1997, now U.S. Pat. No. 6,277,976, which is a 371 of PCT/EP95/03247, filed Aug. 16, 1995.

BACKGROUND OF THE INVENTION

1. Field of the Invention

This invention relates to cellular nuclear receptors.

2. Brief Description of the Art

A large family of nuclear receptors has been identified which confer cells with responsiveness to molecules such as retinoic acid, vitamin D3, steroid hormones and thyroid hormones. Extensive studies have shown that the members of this superfamily of nuclear receptors activate and/or repress gene transcription through direct binding to discrete cis- acting elements termed "hormone response elements" (HRE). It has been shown that these HRE's comprise repeats of consensus palindromic hexanucleotide DNA motifs. The specificity of the HRE's is determined by the orientation of, and spacing between, halfsites (i.e. half a palindromic sequence)(Umenesono K., et al, 1991 Cell 65, 1255–1266).

Specific DNA binding is mediated by a distinct DNA binding domain, containing two zinc fingers, which is conserved among all thus discovered nuclear receptors. three amino acids at the C-terminal base of the first zinc finger (known as the "P-box") are important for the recognition of the half site nucleotide sequence. Members of the nuclear receptor superfamily have been classified into different groups on the basis of an amino acid sequence within the P box.

Molecules thought to be nuclear receptors, as they are structurally related to characterized receptors, but for which no ligand has been identified are termed "orphan receptors". Many such orphan receptors have been identified (see for example Evans R. M, (1988) *Science* 240,889–895 and O'Malley, B. (1990) *Mol. Endocrinol.* 4 363–369).

BRIEF SUMMARY OF THE INVENTION

According to one aspect of the invention there is provided a novel nuclear receptor, hereinafter terms "OR-1", having the amino acid sequence of FIG. 1 (SEQ ID NO:2) or substantially the same amino acid sequence as the amino acid sequence shown in FIG. 1 (SEQ ID NO:2) or an amino acid sequence functionally similar to that sequence.

An amino acid sequence which is more than about 90%, preferably more than 95%, identical with the sequence shown in FIG. 1 (SEQ ID NO:2) is substantially the same amino acid sequence for the purposes of the present application.

According to another aspect of the invention there is provided a DNA sequence encoding a nuclear receptor according to the first aspect of the invention. Preferably, the DNA sequence is that given in FIG. 2 (SEQ ID NO:1) or is a DNA sequence encoding a protein or polypeptide having the functionality of OR-1.

The nuclear receptor of the invention has a similar P-box configuration to the retinoic acid receptor (RAR), the vitamin D receptor (VDR), and the thyroid hormone receptor (TR) and can be placed in the same subfamily as those receptors.

Preferably, the receptor heterodimerizes with RXR to form a complex.

Preferably, the receptor interacts with RXR and binds to a DNA sequence comprising at least one repeat of the DNA sequence AGGTCA (SEQ ID NO:10. Preferably the sequence is AGTCAGGTCACTCGAGGTCAGTCA (SEQ ID NO:11)

Preferably, the receptor modulates 9-cis retinoic acid signalling.

BRIEF DESCRIPTION OF THE DRAWINGS

The nuclear receptor of the invention, OR-1, and its method of production will now be described, by way of example only, with reference to the accompanying drawings FIGS. 1–5, in which:

FIG. 1 shows the amino acid sequence of a nuclear receptor of the invention (SEQ ID NO:2);

FIGS. 2A and 2B show the DNA sequence of a nuclear receptor of the invention (SEQ ID NO:1);

FIG. 5A gives the DNA sequences of seven potential HRE's DR-0–DR-6;

DETAILED DESCRIPTION OF THE INVENTION

Cloning and Expression of OR-1

Figure 3:
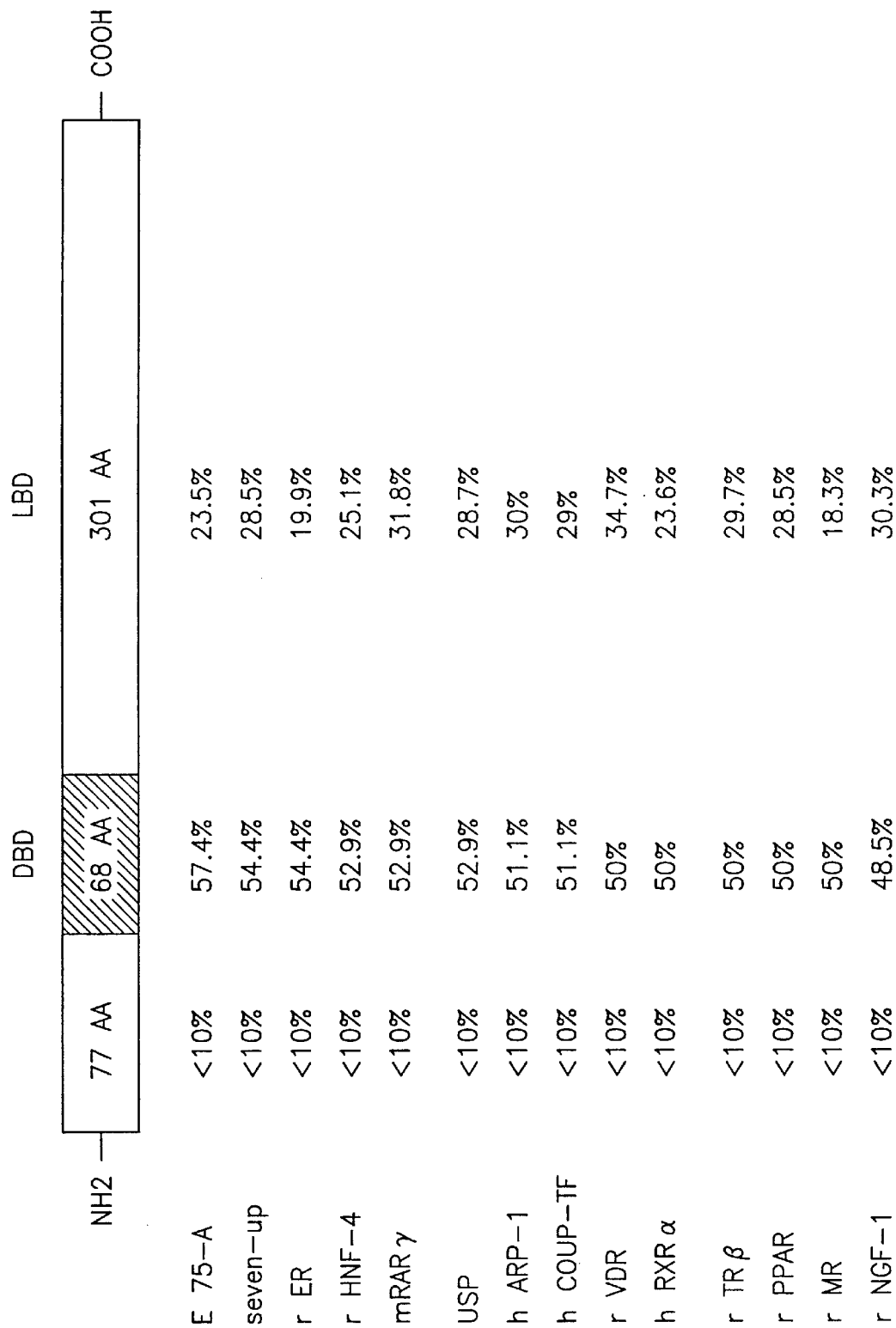
FIG. 3 gives a comparison between the primary amino acid sequences of the nuclear receptor of the invention and those of other members of the nuclear receptor superfamily.

Rat OR-1 was cloned from a cDNA library from Sprague Dawley rat liver in the commercially-available λZAP vector (Stratagene, USA) using the techniques described in Gottlicher, M. et al (1992) *Proc. Natl. Acad. Sci. USA* 89, 4653–4657.

Foetal and adult rat tissues were excised after decapitation and frozen on dry ice. Cryostat sections were hybridized to 48-mer oligonucleotides complementary to OR-1 mRNA positions 100–151 and 850–900 as described in Dagerlind, A et al (1992) *Histochemistry* 98 34–49.

Several unrelated oligonucleotides were also used as controls. The addition of 100 fold of the respective nonlabelled control oligonucleotide abolished all labelling observed with the OR-1 probes.

Plasmids

OR-1 cDNA was subcloned as a Eco RI fragment in pGEM-3Z (Promega) to produce the plasmid pROR-1-Sp6, or in the multiple cloning site of pCMV5 (described in Andersson, S. et al 1989 *J. Biol. Chem.*, 264, 8222–8229) to produce the plasmid pCMV-OR-1. The reporter construct pDR4-AF contains a SphI-XhoI fragment of the cDNA for a secreted form of human PAP (placental alkaline phosphatase) described in (Berger, J. et al. 1998 *Gene* 66,1 −10) under the control of a DR4-TK-containing promoter, pRRXR-T7 and pCMV-RXR described previously in Gearing, K. L. et al 1993 *Proc. Natl. Acad. Sci USA* 90, 1440–1444.

DNA Binding Studies

Gel shifts were performed using in vitro-translated OR-1 and RXR with the commercially-available TNT™-coupled reticulocyte lysate system (Promega, Madison USA). Proteins were incubated on ice for 15 min with 4 μg of poly (dI-dC) and with unlabelled competitor DNA where indicated in a solution comprising 100 mM KCI; 10 mM Hepes,pH7.6; 1 mM dithiothreitol; 1 mM EDTA; 10% (wt./vol) glycerol, before addition of 0.5 ng of a $^{32}$P-end labelled oligonucleotide probe. The reaction mixtures were incubated for a further 10 min at 22° C. before electrophoresis at 200V and 4° C. in pre-run 4% polyacryliamide/0.25 TBE (0.089 m tris-borate pH 8.3, 0.025 EDTA) gels.

The following oligonucleotides and their complements were used as probes:

| DR0 | AGCTTCAGGTCAAGGTCAGGTTCA | (SEQ ID NO:3) |
|---|---|---|
| DR1 | AGCTTAGGTCACCAGGTCAGTTCA | (SEQ ID NO:4) |
| DR2 | AGCTTAGGTCACCAGGTCAGTTCA | (SEQ ID NO:5) |
| DR3 | AGTCAGGTCACTCGAGGTCAGTCA | (SEQ ID NO:6) |
| DR4 | AGTCAGGTCACTCGAGGTCAGTCA | (SEQ ID NO:7) |
| DR5 | AGTCAGGTCACTCGTAGGTCAGTCA | (SEQ ID NO:8) |
| DR6 | AGTCAGGTCACTCGTTAGGTCAGTCA | (SEQ ID NO:9) |

Cells and Transfection

Embryonal carcinoma P19 EC cells were cultured in Dulbecco's modified Eagle's medium supplemented with 10% foetal calf serum, nonessential amino acids, penicillin (100 units/ml) and streptomycin (100 mg/ml). Chinese Hamster Ovary (CHO) cells were cultured in Ham's F-12 medium supplemented with 10% foetal calf serum, penicillin (100 units/ml) and streptomycin (100 mg/ml). Cells were plated in duplicate in 35 mm Petri dishes and transfected at 30% confluency, using lipofectin reagent (Bethesada Research Laboratories, USA) according to the recommendations of the supplier. After 12 hours the medium was changed and supplemented or not supplemented as the case may be with 100 nM 9-cis retinoic acid (a gift of Hoffman-LaRoche) as indicated, and incubated for an additional 36 h. Cell culture supernatants were then heated to 65° C. for 30 min. PAP activity was determined as the increase in $A_{405}$ at 30° C. in a 1 ml reaction mixture containing 0.75 ml of supernatant, 200 nM Tris (pH8.8), 275 nM NaCl, 0.5 mM $MgCl_2$, and 5 mM p-nitrophenylphosphate.

Transfections were repeated 6 times with different plasmid preparations and data from a representative experiment is presented here.

Results

The OR-1 clone spans 1940 bp including a 55 bp long poly-A tail and contains an open reading frame starting with an ATG corresponding to a protein of 446 amino acids with a predicted molecular weight of 50 kD. The complete amino acid and nucleotide sequences of OR-1 are given in FIGS. 1 and [2] FIGS. 2A and 2B (SEQ ID NO:2 and SEQ ID NO:1) respectively. OR-1 shows no striking homology to known members of the nuclear receptors superfamily: the highest homologies represent less than 10% in the N-terminal domain, about 50% in the DNA binding domain, and between 20–30% in the putative ligand binding domain as shown in FIG. 3. The amino-terminal domain of OR-1 (underlined in FIG. 1 (SEQ ID NO:1)) is 77 amino acids long and to a large extent comprises a so-called "PEST" sequence, meaning that it is an amino acid sequence rich in proline, glutamic acid, serine, threonine, and aspartic acid residues.

The DNA binding domain consists of 68 amino acids including the nine invariable cysteines characteristic of the members of the nuclear receptor superfamily, as well as other amino acids that are found to be conserved in all members of this protein family.

Genomic Cloning

A rat genomic fragment has been isolated, that spans the DNA binding domain of OR1 and all the exons downstream of it. Most nuclear receptors for which the genomic structure has been determined have the two zinc "fingers" of the DNA binding domain encoded on separate exons. We have shown that the whole DNA-binding domain is encoded by one exon in OR1. We have furthermore shown that this is also the case with RLD-1 (Mol. Endocrinol. infra), a closely related receptor "knock-out" mice of OR1 and RLD-1.

Tissue Distribution of OR-1

Figure 4:
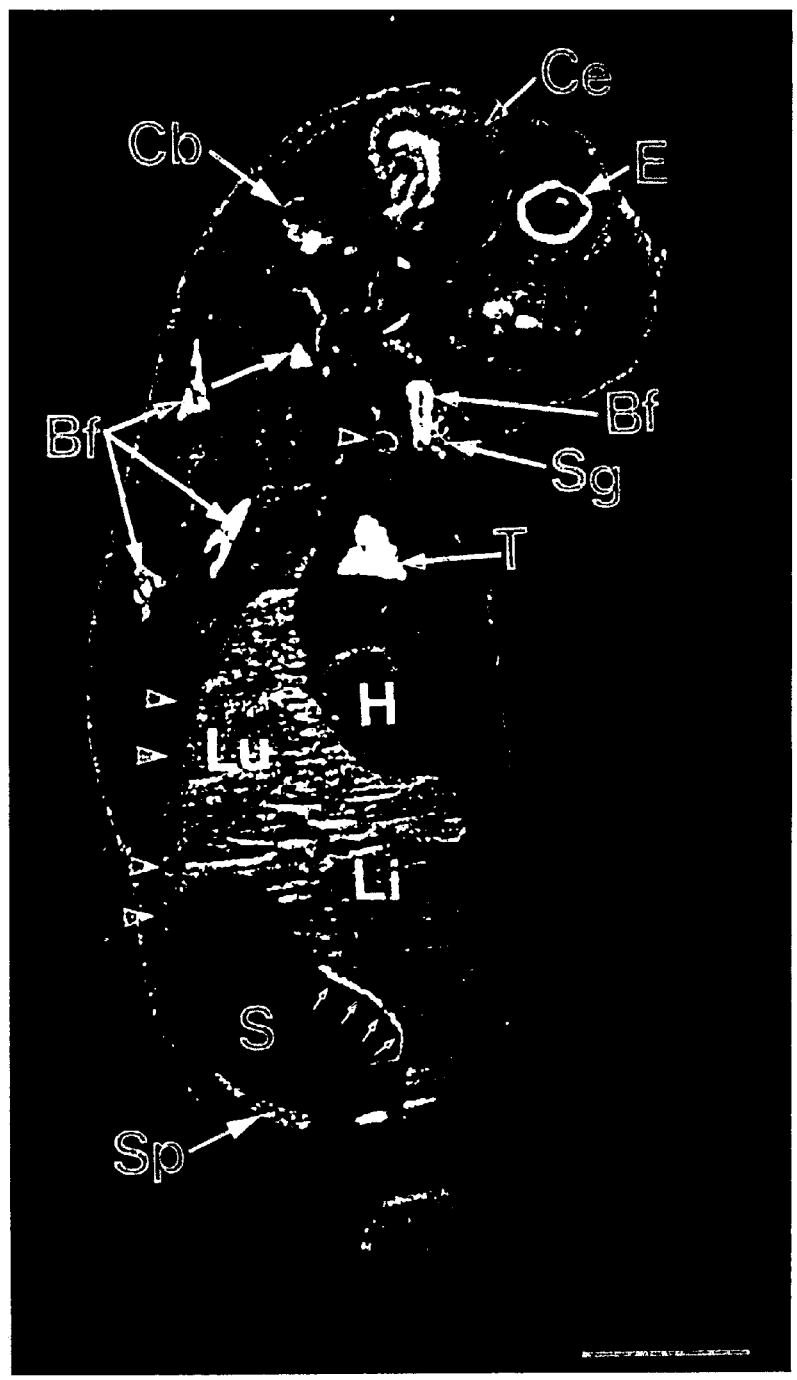
FIG. 4 Localization of OR-1 mRNA-producing cells in rat tissues with in situ hybridization.

To analyse the tissue distribution of OR-1 transcripts, in situ hybridizations were performed on foetal and adult rat tissues. Labelling for OR-1 was found in several tissues of both foetal and adult rats. As discussed, below, prominent expression was observed in liver, lung, thymus, brown fat, salivary gland, thyroid gland, pituitary gland and retina whereas moderate levels were seen in developing cerebrum and cerebellum, in perichondrium around developing bones, heart and skin. Low levels of OR-1 mRNA was present in skeletal muscle as shown in FIG. 4. In adult rats, strong labelling was found in lymph node, prostate, adrenal cortex and the intermediate lobe of the pituitary gland. Moderate levels were seen in liver, testis, salivary gland, thyroid and parathyroid gland, adrenal medulla, anterior pituitary and kidney. In the brain, a moderate signal was observed in neurons in the granular cell layer of the cerebellum and hippocampus.

1) Immune System

Prominent expression of OR-1 mRNA was seen in the cortex of the thymus with lower levels in the medulla. In dipped sections grains were seen over most of the thymocytes in the cortex. Significant expression was also seen in the lymph nodes, whereas low levels were observed in spleen. Some cells in the bone marrow expressed OR-1 mRNA.

2) Endocrine System

Significant expression of OR-1 was seen in the anterior and intermediate lobes of the pituitary. In dipped sections grains could be seen over most of the cells in the intermediate lobe and over the majority of the cells in the anterior lobe. The posterior lobe appeared virtually nonlabelled. Prominent expression of OR-1 was detected in the parathyroid glands where most of the cells expressed OR-1 mRNA. In the thyroid gland moderate expression was observed and OR-1 mRNA was heterogenously distributed in different cell types. Most of the parafollicular cells expressed OR-1, whereas only part of the follicular cells were labelled. High expression in the adrenal gland was observed in all layers of the cortex, whereas lower levels were seen in the medulla. Expression of OR-1 was slightly higher in the zona glomerulosa than in the rest of the cortex. In the adrenal medulla the labelling was hererogenous and part of the chromaffin cells and ganglion cells expressed OR-1. In pineal gland some cells ontained OR-1 mRNA.

3) Reproductive System

OR-1 could be detected both in male and female genital organs. In the testis

OR-1 mRNA was present in all cross-sections of the seminiferous tubules. The labelling localizes to the basal compartment of the seminiferous epithelium and grains could be seen mainly over primary spermatocytes, whereas spermatogonia and germ cells at later developmental stages were non-labelled. The Sertoli cells and Leydig cells did not express OR-1 mRNA. A strong signal for OR-1 was evident in the epithelium of the prostate gland and also in the epididymis, whereas low levels were seen in the epithelium of the vesicula seminalis. In the ovary oocytes at different states of development expressed OR-1 mRNA while other cells appeared non-labelled. In the uterus the epithelium was strongly labelled and lower levels of OR-1 mRNA were seen in the myometrium.

4) Urinary System

Moderate expression of OR-1 could be detected in the outer medulla of the kidney, whereas in the cortex and inner medulla the labelling was very low or nondetectable. In dipped sections grains were seen over different parts of the loop of Henle. The glomeruli, proximal and distal convoluted tubules and collection tubules did not express OR-1 at detectable levels. The transitional epithelium of the renal pelvis expressed OR-1.

5) Digestive System

In salivary glands the secretory acini and the ducts expressed moderate levels of OR-1 mRNA. In the liver OR-1 mRNA was evenly distributed throughout the liver and most, if not all, hepatocytes were labelled. In the intestinal tract OR-1 was expressed in the epithelium of stomach and small and large intestine.

6) Nervous System

Significant expression of OR-1 was seen in the sympathetic and sensory ganglia. In superior cervical ganglion most of the sympatetic neurons] expressed OR-1 at high level and also the satellite cells were labelled. In dorsal root ganglion the labelling was heterogenous and varied between individual neurons. The Schwan cells of peripheral nerves expressed OR-1 whereas oligodendrocytes in optic nerve were nonlabelled. In the retina the bipolar cells expressed OR-1. In the central nervous system OR-1 mRNA was seen in several areas including hippocampus and cerebellum.

7) Respiratory System

Moderate expression of OR-1 was seen in the bronchial epithelium and in the alveoli.

8) Other Tissues

Low or non-detectable levels of OR-1 were seen in sketal muscle and hear.

Also in white adipose tissue OR-1 expression was below the detection limit. In the skin a clear signal was observed in keratinocytes in the basal part of the epidermis. A strong signal was seen in perichondrium around the cartilage in trachea. Low expression of OR-1 could be seen in intra and extraorbital lacrimal glands.

The expression of OR-1 thus appears to be ubiquitous, suggesting that this receptor might have a house keeping function and/or mediate many effects by regulating the transcriptor of various genes. The tissue distribution or OR-1 is different from the tissue distribution of RLD-1 (*Mol Endocrinol* 9, 72–85, 1995) suggesting that these two isoforms might have different functions. OR-1 is particularly well expressed in tissues involved in the immune system. It has been described that 9-cis retinoic acid plays a role in thymocyte development, being a potent negative regulator of activation-induced T-cell apoptosis. Since OR-1 dimerizes with RXR and is expressed at a high level in the thymus during the fetal stages, it may play a role in regulating T-cells development. OR-1 is also well expressed in peripheral endocrine glands, in male and female genital organs and in the nervous system. The tissue distribution of OR-1 is thus different from that of RXRα which has been described to be noticeably abundant in visceral tissues such as liver, kidney, lung, brain, heart, intestine and testis. We previously suggested that OR-1 could act as a helper of RXRα in mediating the effects of 0-cis retinoic acid. Nevertheless we do not know whether OR-1 could also act as a monomer, as a homodimer or as a heterodimer with another protein thatn RXRα. For example, it is possible that OR-1 modulates the actions of RXRβ that shows a diffuse and probably ubiouitous expression, and of RXRγ which has a more specific distribution.

OR-1 Interacts with RXR on a DR4 Motif In Vitro

A set of potential RE's, DR0–DR6, having the DNA sequences described above predicted by the 3-4-5 rule (Umensono et al supra) was synthesized and assayed in gel shift experiments using in vitro translated OR-1 alone or in combination with RXR also translated in vitro. In vitro translation of OR-1 produced a protein of the predicted size of 50 kD. In the gel shift assays, OR-1 was unable to bind to any of the potential HRE's but OR-1 combined with RXR, recognized the potential HRE DR4 which is usually described as the thyroid hormone response element (TRE) (Umensono et al supra).

Figure 5B:
FIG. 5B illustrates the interaction between OR-1 or the retinoid X receptor (RXR) and the potential HRE's, DR-2 and DR4.
Figure 6:
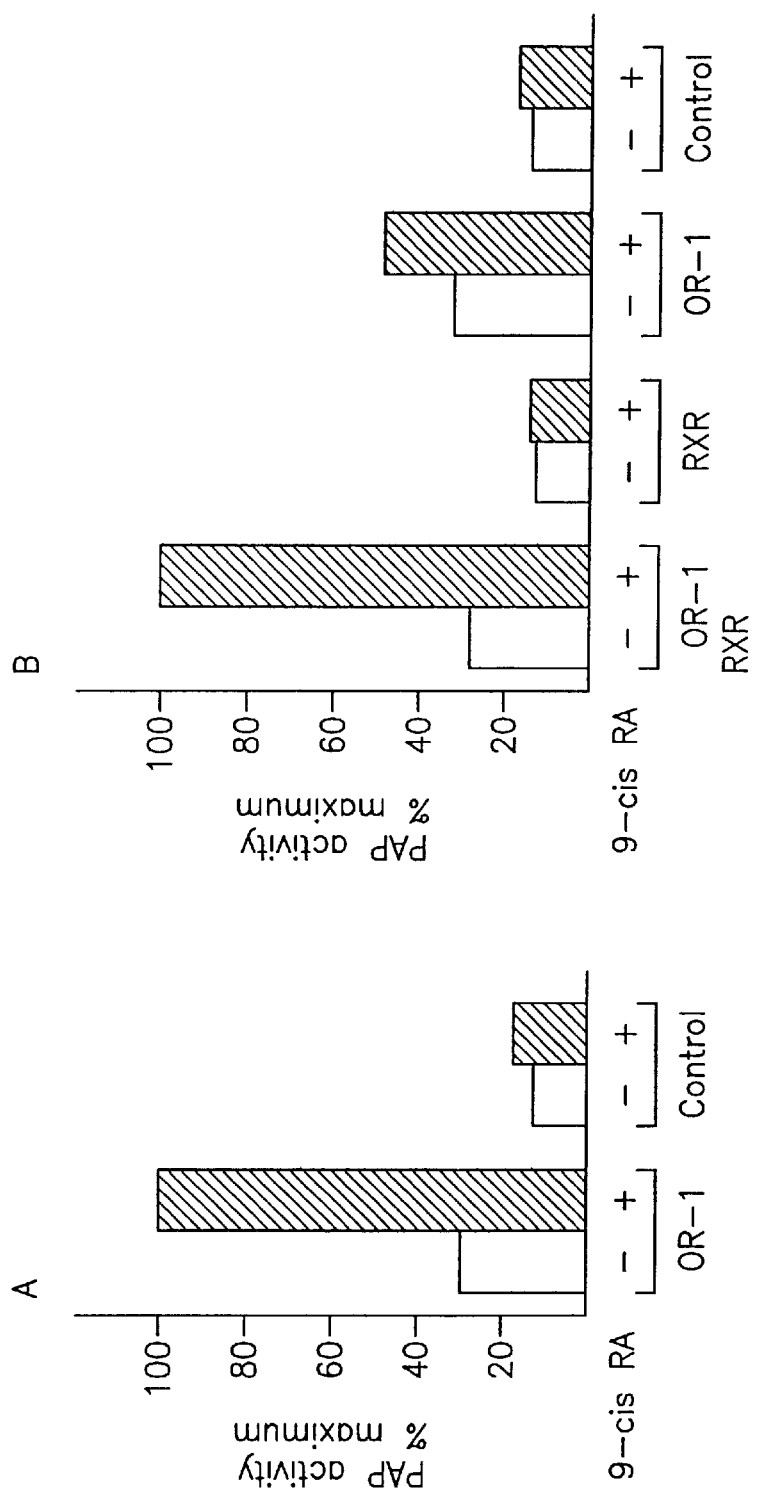
FIG. 6 illustrates experiments showing that OR-1 confers 9-cis retinoic acid-responsiveness of RXR on a DR-4-containing promoter.

FIG. 5B shows that although OR-1 or RXR alone was not able to bind to DR4, together these proteins were able to form a specific complex with this DNA element. The appearance of this complex depends on the presence of RXR and is inhibited by a 10-fold excess of the specific DNA target element, but not by a 100-fold excess of an unrelated DNA element-see FIG. 5B, lane 7)

OR-1 Confers 9-CIS Retinoic Acid Responsiveness of RXR on a DR4-Containing Promoter Since OR-1 and RXR formed a specific complex on the DR4 sequence in vitro, coexpression of OR-1 in embryonal carcinoma (EC) cells that express endogenous RXR was tested to determine whether it could affect the activity of a reporter gene under the control of a DR4-containing promoter. RXR has been shown to be an auxiliary receptor for several classes of hormone receptors, controlling the ligand responses of receptors that form herterodimers with RXR (Yu, V. C. et al 1991 *Cell* 67, 251–1266 and Bugge, T. H. et al 1992 *EMBO J.* 11, 1409–1418). In addition, it has been shown that 9-cis retinoic acid leads to effective RXR homodimer formation and that these homodimers bind and activate several retinoic acid response elements (:RARE's"), but not natural thyroid hormone response element (Zhang, X. K. et al 1993, *J. Biol Chem.* 268, 3825–3828) our transfection studies showed no induction by 9-cis retinoic acid of RXR on a reporter containing DR4 (FIG. 5). Expression o OR-1 allowed activation of RXR by 9-cis retinoic acid on a DR4-containing promoter. In CHO cells that do not express endogenous RXR at as high a level as EC cells, cotransfection of RXR together with OR-1 is necessary to obtain induction by 9-cis retinoic acid. Thus acting as a helper of RXR, OR-1 appears to confer 9-cis retinoic acid signalling on DR4-containing promoters.

What is claimed is:

1. An isolated nucleic acid which codes for a polypeptide consisting of the amino acid sequence of SEQ ID NO:2.

2. The isolated nucleic acid of claim 1, wherein said isolated nucleic acid consists of the nucleic acid sequence of SEQ ID NO:1.

* * * * *

UNITED STATES PATENT AND TRADEMARK OFFICE
CERTIFICATE OF CORRECTION

PATENT NO. : 6,525,188 B2
DATED : February 25, 2003
INVENTOR(S) : Eva L.K. Enmark et al.

It is certified that error appears in the above-identified patent and that said Letters Patent is hereby corrected as shown below:

<u>Title page,</u>
Item [73], Assignee, "Karo Bio Ab" should read -- Karo Bio AB --

Signed and Sealed this

Sixth Day of January, 2004

JAMES E. ROGAN
*Director of the United States Patent and Trademark Office*